United States Patent
Grashow et al.

(10) Patent No.: US 12,083,274 B2
(45) Date of Patent: Sep. 10, 2024

(54) SYSTEM AND METHOD FOR INCREASING ADHERENCE TO A PRESSURE SUPPORT THERAPY

(71) Applicant: KONINKLIJKE PHILIPS N.V., Eindhoven (NL)

(72) Inventors: Jonathan Sayer Grashow, Pittsburgh, PA (US); Gregory Delano Matthews, Pittsburgh, PA (US); Michael Thomas Kane, Harrison City, PA (US); Benjamin Irwin Shelly, Pittsburgh, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 534 days.

(21) Appl. No.: 16/456,419

(22) Filed: Jun. 28, 2019

(65) Prior Publication Data
US 2020/0001031 A1    Jan. 2, 2020

Related U.S. Application Data

(60) Provisional application No. 62/691,682, filed on Jun. 29, 2018.

(51) Int. Cl.
*A61M 16/00*   (2006.01)
*A61B 5/00*    (2006.01)
*A61M 16/06*   (2006.01)

(52) U.S. Cl.
CPC ......... *A61M 16/024* (2017.08); *A61B 5/4818* (2013.01); *A61M 16/0051* (2013.01);
(Continued)

(58) Field of Classification Search
CPC ............ A61M 16/024; A61M 16/0051; A61M 16/00; A61M 16/0069; A61M 16/022; A61M 16/021; A61M 2016/0021; A61M 2016/0027; A61M 2205/52; A61M 2205/33; A61M 2205/3303; A61M 2205/3584; A61M 2205/50; A61M 2205/581; A61M 2205/582; A61M 2205/583; A61M 2230/06; A61M 2230/63; A61M 2230/205; A61B 5/4818;
(Continued)

(56) References Cited

U.S. PATENT DOCUMENTS 6,240,921 B1 * 6/2001 Brydon ............. A61M 16/0051
                                                    128/204.18
8,881,727 B2 * 11/2014 Aloia ..................... A61B 5/087
                                                    128/204.23
(Continued)

FOREIGN PATENT DOCUMENTS

JP         2002301048 A     10/2002
WO    WO-2017032873 A2 *   3/2017    ........... A61B 5/7275
WO        2018115216 A1     6/2018

*Primary Examiner* — Samchuan C Yao
*Assistant Examiner* — Sarah B Lederer (57) ABSTRACT

A method for increasing adherence of a patient to a therapy provided by a pressure support device includes: collecting data regarding a number of attributes of the patient along with time information thereof; determining the occurrence of a sleep-related event from the data; determining a condition of the pressure support device; and providing an indication to the patient responsive to determining the occurrence and determining the condition.

20 Claims, 2 Drawing Sheets

(52) U.S. Cl.
CPC .... *A61M 16/0069* (2014.02); *A61M 16/0622* (2014.02); *A61B 5/4812* (2013.01); *A61B 5/4815* (2013.01); *A61M 2205/52* (2013.01)

(58) Field of Classification Search
CPC ....... A61B 5/4812; A61B 5/4815; A61B 5/08; A61B 5/0205; A61B 2505/07; G16H 20/40
See application file for complete search history.

(56) References Cited

U.S. PATENT DOCUMENTS

| | | | | |
|---|---|---|---|---|
| 2004/0187871 A1* | 9/2004 | Kimmel | ............... | A61B 5/4833 128/204.23 |
| 2005/0061315 A1* | 3/2005 | Lee | ...................... | A61B 5/0031 128/200.24 |
| 2005/0061319 A1* | 3/2005 | Hartley | ................ | A61B 5/4812 128/204.23 |
| 2011/0100366 A1* | 5/2011 | Chou | .................. | A61B 5/0205 128/204.23 |
| 2015/0133809 A1* | 5/2015 | Paul | .................. | A61M 16/0003 128/205.25 |
| 2015/0290406 A1* | 10/2015 | Bertinetti | .............. | A61M 16/16 128/202.22 |
| 2016/0193437 A1* | 7/2016 | Bao | ........................ | A45C 3/001 128/203.14 |
| 2016/0270717 A1* | 9/2016 | Luna | .................... | A61B 5/743 |
| 2016/0270718 A1* | 9/2016 | Heneghan | .............. | G16H 50/20 |
| 2017/0348498 A1* | 12/2017 | Salter | .................... | A61M 16/16 |

* cited by examiner

SYSTEM AND METHOD FOR INCREASING ADHERENCE TO A PRESSURE SUPPORT THERAPY

BACKGROUND OF THE INVENTION

1. Field of the Invention

The present invention pertains methods for increasing adherence to prescribed therapies, and, more particularly, to methods for increasing adherence to prescribed pressure support therapies. The present invention also relates to systems for use in carrying out such methods.

2. Description of the Related Art

Many individuals suffer from disordered breathing during sleep. Sleep apnea is a common example of such sleep disordered breathing suffered by millions of people throughout the world. One type of sleep apnea is obstructive sleep apnea (OSA), which is a condition in which sleep is repeatedly interrupted by an inability to breathe due to an obstruction of the airway; typically the upper airway or pharyngeal area. Obstruction of the airway is generally believed to be due, at least in part, to a general relaxation of the muscles which stabilize the upper airway segment, thereby allowing the tissues to collapse the airway. Another type of sleep apnea syndrome is a central apnea, which is a cessation of respiration due to the absence of respiratory signals from the brain's respiratory center. An apnea condition, whether obstructive, central, or mixed, which is a combination of obstructive and central, is defined as the complete or near cessation of breathing, for example a 90% or greater reduction in peak respiratory air-flow.

Those afflicted with sleep apnea experience sleep fragmentation and complete or nearly complete cessation of ventilation intermittently during sleep with potentially severe degrees of oxyhemoglobin desaturation. These symptoms may be translated clinically into extreme daytime sleepiness, cardiac arrhythmias, pulmonary-artery hypertension, congestive heart failure and/or cognitive dysfunction. Other consequences of sleep apnea include right ventricular dysfunction, carbon dioxide retention during wakefulness, as well as during sleep, and continuous reduced arterial oxygen tension. Sleep apnea sufferers may be at risk for excessive mortality from these factors as well as by an elevated risk for accidents while driving and/or operating potentially dangerous equipment.

Even if a patient does not suffer from a complete or nearly complete obstruction of the airway, it is also known that adverse effects, such as arousals from sleep, can occur where there is only a partial obstruction of the airway. Partial obstruction of the airway typically results in shallow breathing referred to as a hypopnea. A hypopnea is typically defined as a 50% or greater reduction in the peak respiratory air-flow. Other types of sleep disordered breathing include, without limitation, upper airway resistance syndrome (UARS) and vibration of the airway, such as vibration of the pharyngeal wall, commonly referred to as snoring.

It is well known to treat sleep disordered breathing by applying a continuous positive air pressure (CPAP) to the patient's airway. This positive pressure effectively "splints" the airway, thereby maintaining an open passage to the lungs. It is also known to provide a positive air pressure (PAP) therapy in which the pressure of gas delivered to the patient varies with the patient's breathing cycle, or varies with the patient's breathing effort, to increase the comfort to the patient. This pressure support technique is referred to as bi-level pressure support, in which the inspiratory positive airway pressure (IPAP) delivered to the patient is higher than the expiratory positive airway pressure (EPAP). It is further known to provide a positive pressure therapy in which the pressure is automatically adjusted based on the detected conditions of the patient, such as whether the patient is experiencing an apnea and/or hypopnea. This pressure support technique is referred to as an auto-titration type of pressure support, because the pressure support device seeks to provide a pressure to the patient that is only as high as necessary to treat the disordered breathing.

Pressure support therapies as just described involve the placement of a patient interface device including a mask component having a soft, flexible sealing cushion on the face of the patient. The mask component may be, without limitation, a nasal mask that covers the patient's nose, a nasal/oral mask that covers the patient's nose and mouth, or a full face mask that covers the patient's face. Such patient interface devices may also employ other patient contacting components, such as forehead supports, cheek pads and chin pads. The patient interface device is typically secured to the patient's head by a headgear component. The patient interface device is connected to a gas delivery tube or conduit and interfaces the pressure support device with the airway of the patient, so that a flow of breathing gas can be delivered from the pressure/flow generating device to the airway of the patient.

Despite many innovations in devices use for providing a pressure support therapy, therapy adherence remains a challenge for a significant portion of patients for which such treatments are prescribed.

SUMMARY OF THE INVENTION

Accordingly, it is an object of the present invention to provide systems and methods that increase adherence to prescribed pressure support therapies.

As one aspect of the invention, a method for increasing adherence of a patient to a therapy provided by a pressure support device is provided. The method comprises: collecting data regarding a number of attributes of the patient along with time information thereof; determining the occurrence of a sleep-related event from the data; determining a condition of the pressure support device; and providing an indication to the patient responsive to determining the occurrence and determining the condition.

Collecting data regarding a number of attributes of the patient may comprise collecting data regarding one or more of: actigraphy, heart rate, and/or oxygen saturation of the patient.

Determining the occurrence of a sleep event may comprise determining one or more of: a pre-determined bed time for the patient will be occurring within a predetermined period of time; the patient is trailing toward sleep; the patient is sleeping; and/or the patient is experiencing a sleep disruption.

Determining a condition of the pressure support device may comprise determining that the pressure support device is one of turned on and in use or not turned on.

Determining a condition of the pressure support device may comprise determining that the pressure support device is one of: not within a predetermined proximity of the patient; within a predetermined proximity of the patient, turned on and in use; or within a predetermined proximity of the patient but not turned on.

Determining the occurrence of a sleep-related event from the data may comprise determining sleep onset by the patient and the occurrence of a sleep disruption; wherein determining a condition of the pressure support device comprises determining the pressure support device is not in use; and providing an indication to the patient responsive to determining the occurrence and determining the condition comprises providing an audible alert and providing a visual alert to use the pressure support device.

Determining the occurrence of a sleep-related event from the data may comprise determining that a bed time for the patient will be occurring within a predetermined period of time; determining a condition of the pressure support device may comprise determining that the pressure support device is not within a predetermined proximity; and providing an indication to the patient may comprise displaying a visual reminder to the patient to obtain the pressure support device for use during sleep.

Determining the occurrence of a sleep-related event from the data may comprise determining that a bed time for the patient will be occurring within a first predetermined period of time; determining a condition of the pressure support device may comprise determining that the pressure support device is within a predetermined proximity and that the patient has not used the pressure support device within another predetermined period of time; and providing an indication to the patient may comprise displaying a visual reminder to the patient that the pressure support device should be used regularly.

Determining the occurrence of a sleep-related event from the data may comprise determining that a bed time for the patient will be occurring within a first predetermined period of time and that the patient is trailing toward sleep; determining a condition of the pressure support device may comprise determining that the pressure support device is not in use; and providing an indication to the patient may comprise providing one or more of an: audible alert, a vibratory alert, and/or a visual alert to the user.

As another aspect of the invention, an external device for use in a system for increasing adherence of a patient to a pressure support therapy is provided. The external device comprises: a number of sensors structured to sense one or more attributes of the patient; a processing unit in communication with the number of sensors; a communications unit in communication with the processing unit, the communications unit being structured to wirelessly communicate with a pressure support device; and an output device structured to provide one or more of a visual, an audible, and/or a vibratory alert to the patient, wherein the processing unit is programmed to: collect data regarding a number of attributes of the patient along with time information thereof; determine the occurrence of a sleep-related event from the data; determine a condition of the pressure support device; and provide an indication via the output device to the patient responsive to determining the occurrence and determining the condition.

The communications unit may be structured to wirelessly communicate with the pressure support device via a Bluetooth™ standardized protocol for sending and receiving data via a wireless link.

As yet another aspect of the invention, a system for increasing adherence of a patient to a pressure support therapy. The system comprises: a pressure support device; and an external device comprising: a number of sensors structured to sense one or more attributes of the patient; a processing unit in communication with the number of sensors; a communications unit in communication with the processing unit and wirelessly in communication with the pressure support device; and an output device structured to provide one or more of an audible alert and/or a vibratory alert to the patient. The processing unit is programmed to: collect data regarding a number of attributes of the patient along with time information thereof; determine the occurrence of a sleep-related event from the data; determine a condition of the pressure support device; and provide an indication via the output device to the patient responsive to determining the occurrence and determining the condition.

The one or more attributes may comprise at least one of actigraphy or heart rate.

The communications unit may be structured to wirelessly communicate with the pressure support device via a Bluetooth™ standardized protocol for sending and receiving data via a wireless link.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

As used herein, the singular form of "a", "an", and "the" include plural references unless the context clearly dictates otherwise. As used herein, "and/or" shall mean one or both of the elements which are separated by such phrase (e.g., A and/or B would mean A, B, or both of A and B). As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to maintain a constant, fixed orientation relative to each other. As used herein, "selectively coupled" means that two components are coupled in a manner which allows for the components to be readily coupled or uncoupled in a predictable, repeatable manner without damaging either of the components. Unless particularly described otherwise herein, any components which are described merely as being "coupled", may also be "fixedly" or "selectively" coupled without varying from the scope of the present invention.

As used herein, the word "unitary" means a component is created as a single piece or unit. That is, a component that includes pieces that are created separately and then coupled together as a unit is not a "unitary" component or body. As used herein, the statement that two or more parts or components "engage" one another shall mean that the parts exert a force against one another either directly or through one or more intermediate parts or components. As used herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
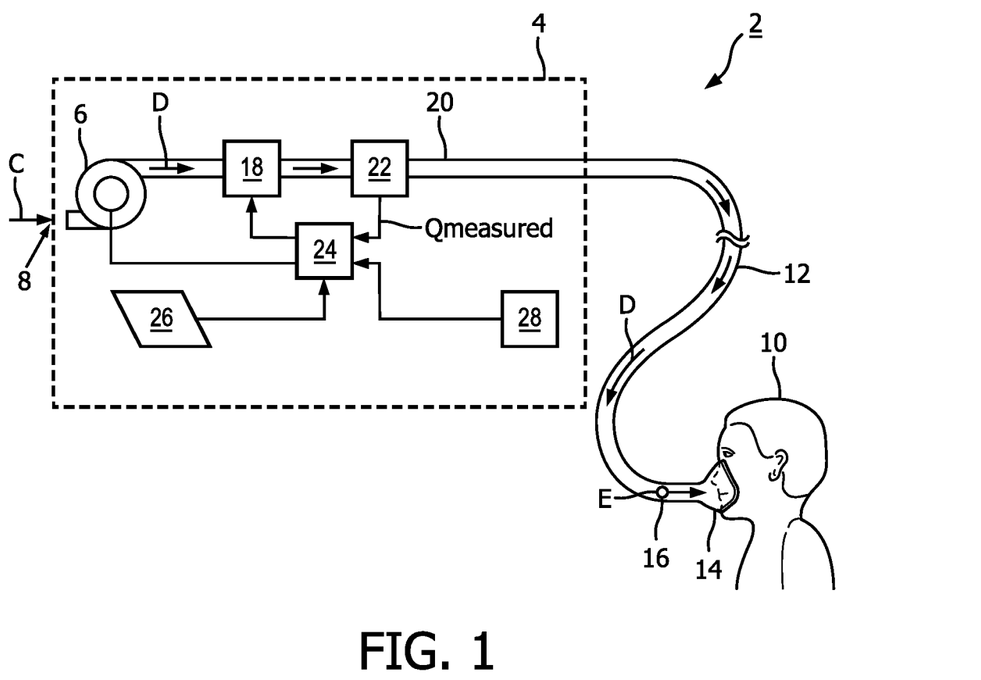
FIG. 1 is a partially schematic view of an airway pressure support system including a pressure generating device in accordance with one example embodiment of the present invention.

An example airway pressure support system 2 which may be employed as a portion of one particular, non-limiting exemplary embodiment of the present invention is shown in FIG. 1. Airway pressure support system 2 includes a pressure support device 4 which houses a blower assembly 6, an example of which will be described in further detail below. Blower assembly 6 receives breathing gas, generally indicated by arrow C, from the ambient atmosphere through a filtered air inlet 8 provided as part of pressure support device 4, and generates a flow of breathing gas therefrom for delivery to an airway of a patient 10 at relatively higher and lower pressures, i.e., generally equal to or above ambient atmospheric pressure, to generate pressure to provide pressure compensation to patient 10 via a patient circuit 12, 14. In the exemplary embodiment, blower assembly 6 is capable of providing a flow of breathing gas ranging in pressure from 2-30 cmH2O. The pressurized flow of breathing gas from blower assembly 6, generally indicated by arrow D, is delivered via a delivery conduit 12 to a breathing mask or patient interface 14 of any known construction, which is typically worn by or otherwise attached to patient 10 to communicate the flow of breathing gas to the airway of patient 10. Delivery conduit 12 and patient interface device 14 are typically collectively referred to as the patient circuit.

Pressure support system 2 shown in FIG. 1 is what is known as a single-limb system, meaning that the patient circuit includes only delivery conduit 12 connecting patient 10 to pressure support system 2. As such, an exhaust vent 16 is provided in delivery conduit 12 for venting exhaled gases from the system as indicated by arrow E. It should be noted that exhaust vent 16 can be provided at other locations in addition to or instead of in delivery conduit 12, such as a location at the patient interface device 14. It should also be understood that exhaust vent 16 can have a wide variety of configurations depending on the desired manner in which gas is to be vented from pressure support system 2.

The present concept also contemplates that pressure support system 2 can be a two-limb system, having a delivery conduit and an exhaust conduit connected to patient 10. In a two-limb system (also referred to as a dual-limb system), the exhaust conduit carries exhaust gas from patient 10 and includes an exhaust valve at the end distal from patient 10. The exhaust valve in such an embodiment is typically actively controlled to maintain a desired level or pressure in the system, which is commonly known as positive end expiratory pressure (PEEP).

Furthermore, in the illustrated exemplary embodiment shown in FIG. 1, patient interface 14 is a nasal/oral mask. It is to be understood, however, that patient interface 14 can include a nasal mask, nasal pillows, a tracheal tube, an endotracheal tube, or any other device that provides a suitable gas flow communicating function. Also, for purposes of the present invention, the phrase "patient interface" can include delivery conduit 12 and any other structures that couple the source of pressurized breathing gas to patient 10.

In the illustrated embodiment, pressure support system 2 includes a pressure controller in the form of a valve 18 provided in internal delivery conduit 20 provided in a housing of pressure support device 4. Valve 18 controls the pressure of the flow of breathing gas from blower assembly 6 that is delivered to patient 10. For present purposes, blower assembly 6 and valve 18 are collectively referred to as a pressure generating system because they act in concert to generate and control the pressure and/or flow of gas delivered to patient 10. However, it should be apparent that other techniques for controlling the pressure of the gas delivered to patient 10, such as varying the speed of blower assembly 6, either alone or in combination with a pressure control valve, are contemplated by the present invention. Thus, valve 18 is optional depending on the technique used to control the pressure of the flow of breathing gas delivered to patient 10. If valve 18 is eliminated, the pressure generating system corresponds to blower assembly 6 alone, and the pressure of gas in the patient circuit is controlled, for example, by controlling the speed of blower assembly 6.

Pressure support system 2 further includes a flow sensor 22 that measures the flow of the breathing gas within delivery conduit 20 and delivery conduit 12. In the particular embodiment shown in FIG. 1, flow sensor 22 is interposed in line with delivery conduits 20 and 12, most preferably downstream of valve 18. Pressure support system 2 additionally includes a pressure sensor 28 that detects the pressure of the pressurized fluid in delivery conduit 20. While the point at which the flow is measured by flow sensor 22 and the pressure is measured by pressure sensor 28 are illustrated as being within pressure support device 4, it is to be understood that the location at which the actual flow and pressure measurements are taken may be anywhere along delivery conduits 20 or 12. The flow of breathing gas measured by flow sensor 22 and the pressure detected by pressure sensor 28 are provided to a processing unit 24 to determine the flow of gas at patient 10 ($Q_{PATIENT}$).

Processing unit 24 includes a processing portion which may be, for example, a microprocessor, a microcontroller or some other suitable processing device, and a memory portion that may be internal to the processing portion or operatively coupled to the processing portion and that provides a storage medium for data and software executable by the processing portion for controlling the operation of pressure support system 2. Processing unit 24 is structured to receive outputs of one or more sensors, such as those previously discussed, which are structured to gather data related to effectiveness of the pressure support therapy. Processing unit 24 is also structured to analyze outputs of the sensors while pressure support therapy is provided to the patient to determine patient airflow and pressure waveforms in the patient circuit.

An input/output device 26 is provided for setting various parameters used by pressure support system 2, as well as for displaying and outputting information and data to a user, such as a clinician or caregiver.

Figure 2:
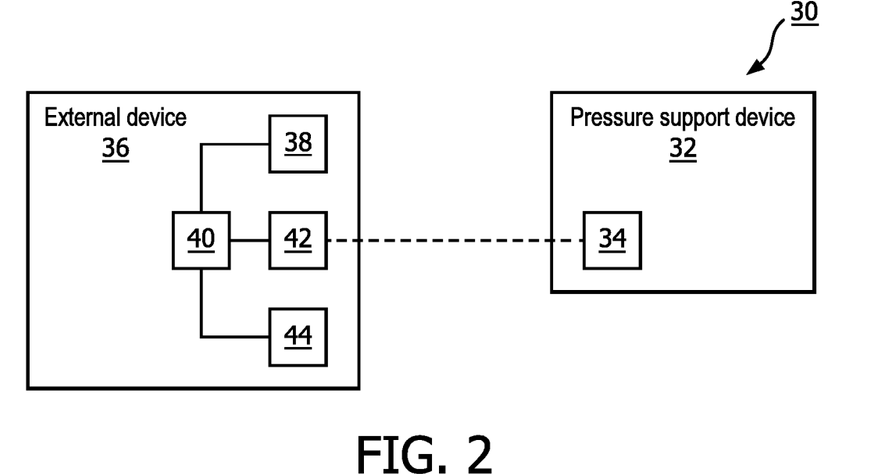
FIG. 2 is a schematic view of a system for use in carrying out methods for increasing adherence to prescribed pressure support therapies in accordance with one example embodiment of the present invention.

An example system 30 for use in carrying out methods for increasing adherence to prescribed pressure support therapies in accordance with one example embodiment of the present invention is shown schematically in FIG. 2. System 30 includes a pressure support device 32 having a processing unit 34, such as pressure support device 4 and processing unit 24 thereof previously described in conjunction with FIG. 1, and an external device 36 in wireless communication (e.g., without limitation, via Bluetooth™) with processing unit 34 of pressure support device 32. In example embodiments of the present invention, external device is a wearable smart device such as a smartwatch (e.g., without limitation, a FitBit or similar device) or other suitable wearable device (e.g., ring, necklace, etc.). External device 36 includes: a number of sensors 38 for sensing one or more attributes (e.g., actigraphy, heart rate, SpO2, location (e.g., GPS coordinates, etc.) of a patient wearing the device along with associated time information for such data, a processing unit 40 for receiving data from the number of sensors 38, a communications unit 42 in communication with processing unit 40 for wirelessly communicating (e.g., via Bluetooth™) with other electronic devices (such as processing unit 34 of pressure support device 32), and an output device 44 which is structured to provide one or more of an visual, audible, and/or a vibratory alert to the patient. Processing unit 40 includes a processing portion which may be, for example, a microprocessor, a microcontroller or some other suitable processing device, and a memory portion that may be internal to the processing portion or operatively coupled to the processing portion and that provides a storage medium for data and software executable by the processing portion for controlling the operation of external device 36.

Figure 3:
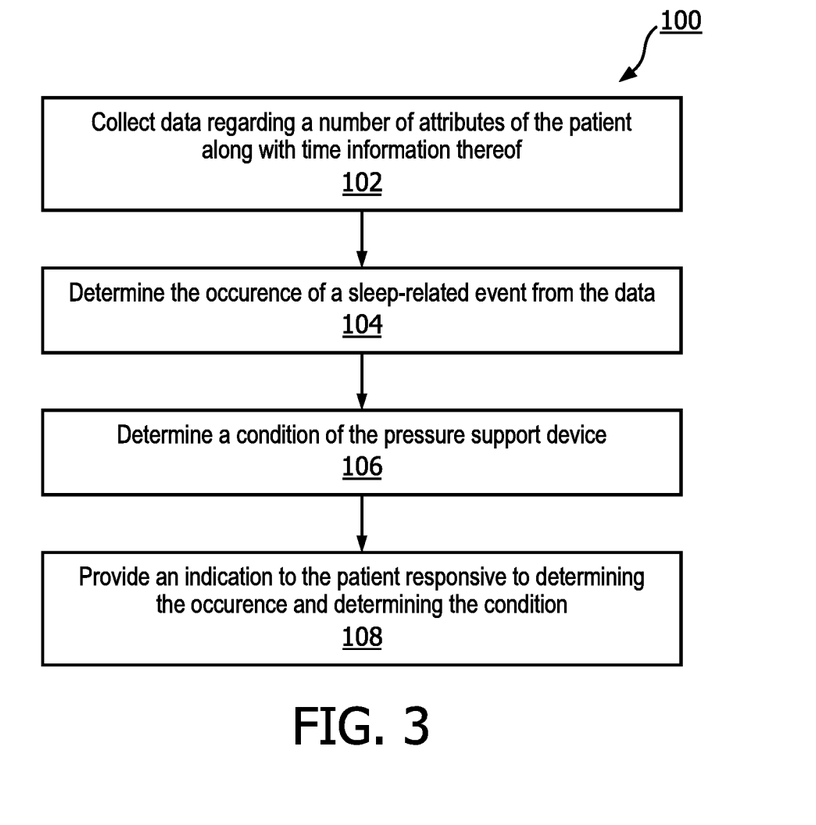
FIG. 3 is a flowchart showing a method for increasing adherence of a patient to a pressure support therapy in accordance with one example embodiment of the present invention.

Having thus described a system 30, an example of a general method 100 in accordance with an example embodiment of the present invention to increase adherence by a patient to a prescribed pressure support therapy provided by a pressure support device 32 of system 30, wherein external device 36 of system 30 is positioned on a patient (e.g., in the form of a watch, necklace, etc.), will now be described in conjunction with FIG. 3. Method 100 begins at 102 wherein data regarding a number of attributes of the patient is sensed/collected by the number of sensors 38 of external device 36. As previously discussed, such data may be of one or more of the patient's actigraphy, heart rate, and/or oxygen saturation, along with time information thereof. Next, the data collected in 102 is analyzed by processing unit 40 in order to determine the occurrence of one or more sleep-related events, such as shown at 104. Such events may include, for example: a pre-determined bed time is nearing (e.g., without limitation, one-hour until the patient's typical bed time as specified by the patient or a caregiver), an expected bedtime (which may be determined from previous bedtimes observed by pressure support device 32), sleep onset (e.g., heart rate variability and/or actigraphy show patient has fallen asleep), and/or sleep disruption (e.g., heart rate variability/accelerations, actigraphy, and/or oxygen desaturation may indicate possible sleep apnea).

At generally the same time (i.e., immediately before, during, or immediately following) the occurrence of a sleep event is determined at 104, a condition of the pressure support device 32 is determined, as shown at 106, via the wireless connection between external device 36 and pressure support device 32. Such determined condition of pressure support device 32 may be that pressure support device is: not within a predetermined proximity of external device 36 and thus the patient who is wearing device 36 (e.g., via GPS, via detecting common wireless network, via Bluetooth™); within a predetermined proximity of external device 36 and thus the patient, while also being turned on and in use; or within a predetermined proximity of the patient but not turned on. Additionally, it may be determined if the pressure support device has been used within a predetermined period of time (e.g., a week) such as via a smartphone phone application or other suitable arrangement tracking usage.

Finally, as shown at 108, an indication is provided to the patient via output device 44 of external device 36. Such indication may be, for example, a visual indication provided on a display, an audio indication provided by a speaker, a vibratory indication, a combination of one or more of the aforementioned, or any other suitable indication depending on the message or urgency thereof.

Having thus described general method 100, some further detailed example embodiments thereof will now be described with continued reference to FIG. 3.

In a first example in accordance with one embodiment of the present invention, sleep onset by the patient and the occurrence of a sleep disruption are determined at 104. Then, at 106, it is determined that the pressure support device is not in use and thus an audible alert (to get the patient's attention) and a visual alert (to inform the patient to use the pressure support device) are provided to the patient at 108.

In another example in accordance with one embodiment of the present invention, it is determined at 104 that a bed time for the patient will be occurring within a predetermined period of time. Next, at 106, it is determined that the pressure support device is not within a predetermined proximity and accordingly, at 108, a visual reminder is provided to the patient to obtain the pressure support device for use during sleep.

In another example in accordance with one embodiment of the present invention, it is determined at 104 that a bed time for the patient will be occurring within a first predetermined period of time. Next, at 106, is it determined that the pressure support device is within a predetermined proximity and that the patient has not used the pressure support device within another predetermined period of time. The patient is then provided with a visual reminder that the pressure support device should be used regularly.

In another example in accordance with one example embodiment of the present invention, it is determined at 104 that a bed time for the patient will be occurring within a first predetermined period of time and that the patient is trailing toward sleep. Next, at 106, it is determined that the pressure support device is not in use. The patient is then provided, at 108, with one or more of: an audible alert, a vibratory alert, and/or a visual alert.

From the foregoing it is to be appreciated that embodiments of the present invention improve adherence and remove some of the common failure modes (excuses) for patients to not use their pressure support device (e.g., "I forgot", "I fell asleep on the couch", "I was reading in bed without my pressure support device and fell asleep", etc.). Benefits for the patient include a better night's sleep, better practice and continuity of their usage of a pressure support device, which will lead to the known health outcomes of compliance with a pressure support therapy (i.e. lowered blood pressure, improved energy, daytime alertness, reduced chance for heart disease etc.).

Features described in this application improve on other concepts of "dumb" set reminders, which can be annoying and easily ignored by a patient (e.g., an alarm saying "put on your CPAP" set for 11 pm every evening). Embodiments of the present invention instead provide actionable guidance (i.e., only alert the user when PAP is available to use) at a time when the user is most likely to need it (i.e., the patient is not wearing the PAP and they are going to sleep) and can be done at times when the user is likely to accept the guidance (e.g., as the patient is actually falling asleep or after they have been awoken from sleep by a SDB event).

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

What is claimed is:

1. A method for interfacing a wearable smart device with a pressure support device for increasing a user adherence to a pressure support therapy provided by the pressure support device, the method comprising:
   collecting, via the wearable smart device worn by the user, data regarding a number of user attributes along with respective time information of the user attributes;
   determining, via the wearable smart device, an occurrence of one or more sleep-related event based on the collected data, wherein the occurrence of the one or more sleep-related event corresponds with at least a need for the pressure support therapy;
   determining, via the wearable smart device in wireless communication with the pressure support device, immediately before, during, and immediately after the occurrence of the one or more sleep-related event, a condition of the pressure support device, wherein determining immediately before the occurrence of the one or more sleep-related events comprises determining that a predetermined bed time for the user will be occurring within a predetermined period of time, and that the pressure support device is within a predetermined proximity of the wearable smart device but not turned on; and
   providing, via the wearable smart device, an actionable guidance indication responsive to the determined occurrence and the determined condition corresponding with (i) the pressure support therapy is needed, (ii) a sleep-related event of the user is falling asleep or is having been awaken from sleep for which the user is likely to accept actionable guidance, and (iii) the pressure support device is located within a given proximity to the wearable smart device, wherein the actionable guidance indication comprises one or more of an audible alert, a vibratory alert, and a visual alert configured to increase the user adherence to the pressure support therapy.

2. The method of claim 1, wherein collecting data regarding the number of user attributes comprises collecting data regarding one or more of:
   actigraphy, heart rate, and/or oxygen saturation of the user and respective time information thereof.

3. The method of claim 1, wherein determining the occurrence of a sleep event further comprises determining one or more of: the user is trailing toward sleep; the user is sleeping; and the user is experiencing a sleep disruption.

4. The method of claim 1, wherein determining, via the wearable smart device in wireless communication with the patient support device, a condition of the pressure support device comprises determining that the pressure support device is (i) one of turned on and in use or (ii) not turned on.

5. The method of claim 1, wherein determining, via the wearable smart device in wireless communication with the patient support device, a condition of the pressure support device further comprises determining that the pressure support device is one of: (i) not within a predetermined proximity of the wearable smart device; or (ii) within the predetermined proximity of the wearable smart device, turned on and in use.

6. The method of claim 1, wherein determining, via the wearable smart device, the occurrence of the sleep-related event based on the collected data comprises determining a sleep onset for the user and an occurrence of a sleep disruption event for the user; wherein determining, via the wearable smart device in wireless communication with the patient support device, the condition of the pressure support device comprises a determination that the pressure support device is not in use; and wherein providing, via the wearable smart device, the actionable guidance indication to the user responsive to the determined occurrence and the determined condition further comprises providing an audible alert and a visual alert as actionable guidance for the user to use the pressure support device.

7. The method of claim 1, wherein determining, via the wearable smart device in wireless communication with the patient support device, the condition of the pressure support device further comprises a determination that the pressure support device is not within a predetermined proximity of the wearable smart device; and
   wherein providing, via the wearable smart device, the actionable guidance indication to the user further comprises displaying, via the wearable smart device, a visual reminder as actionable guidance for the user to obtain, within the predetermined period of time prior to the predetermined bed time, the pressure support device for use during sleep.

8. The method of claim 1, wherein determining, via the wearable smart device in wireless communication with the patient support device, the condition of the pressure support device further comprises a determination that (i) the pressure support device is within a predetermined proximity of the wearable smart device and (ii) the user has not used the pressure support device within a second predetermined period of time; and wherein providing, via the wearable smart device, the actionable guidance indication to the user further comprises displaying, via the wearable smart device, a visual reminder as actionable guidance for the user to use the pressure support device within the second predetermined period of time.

9. The method of claim 1, wherein determining, via the wearable smart device, the occurrence of the sleep-related event based on the collected data further comprises a determination that the user is trailing toward sleep; wherein determining, via the wearable smart device in wireless communication with the patient support device, the condition of the pressure support device further comprises a determination that the pressure support device is not in use; and wherein providing, via the wearable smart device, the actionable guidance indication to the user further comprises providing the one or more of: the audible alert, the vibratory alert, and the visual alert.

10. An external wearable smart device configured to interface with a pressure support device in a system for increasing a user adherence to a pressure support therapy provided by the pressure support device, the external wearable smart device comprising:
   a number of sensors structured to sense, in response to the external wearable device being worn by the user, one or more user attributes;
   a processing unit in communication with the number of sensors;
   a communications unit in communication with the processing unit, wherein the communications unit is structured to wirelessly communicate with the pressure support device; and
   an output device structured to provide one or more of a visual alert, an audible alert, and a vibratory alert, wherein the processing unit is programmed to:
      collect data, via the sensors, regarding a number of user attributes along with respective time information of the user attributes;
      determine an occurrence of one or more sleep-related event based on the collected data, wherein the occurrence of the one or more sleep-related event corresponds with at least a need for the pressure support device therapy;
      determine, via the communications unit in wireless communication with the pressure support device, immediately before, during, and immediately after the occurrence of the one or more sleep-related event, a condition of the pressure support device, wherein determining immediately before the occurrence of the one or more sleep-related events comprises determining that a predetermined bed time for the user will be occurring within a predetermined period of time, and that the pressure support device is within a predetermined proximity of the wearable smart device but not turned on; and
      provide, via the output device, an actionable guidance indication responsive to the determined occurrence and the determined condition corresponding with (i) the pressure support therapy is needed, (ii) a sleep-related event of the user is falling asleep or is having been awaken from sleep for which the user is likely to accept actionable guidance, and (iii) the pressure support device is located within a given proximity to the wearable smart device, wherein the actionable guidance indication comprises one or more of the audible alert, the vibratory alert, and the visual alert configured to increase the user adherence to the pressure support therapy.

11. The external wearable smart device of claim 10, wherein the communications unit is structured to wirelessly communicate with the pressure support device via a Bluetooth™ standardized protocol for sending and receiving data via a wireless link.

12. A system for increasing a user adherence to a pressure support therapy, the system comprising:
   a pressure support device configured to provide the pressure support therapy; and
   an external wearable smart device configured to interface with the pressure support device, wherein the external wearable smart device comprises:
      a number of sensors structured to sense, in response to the external wearable device being worn by the user, one or more user attributes;
      a processing unit in communication with the number of sensors;
      a communications unit in communication with the processing unit and wirelessly in communication with the pressure support device; and
      an output device structured to provide one or more of a visual alert, an audible alert, and a vibratory alert, wherein the processing unit is programmed to:
         collect data, via the sensors, regarding a number of user attributes along with respective time information of the user attributes;
         determine an occurrence of one or more sleep-related event based on the collected data, wherein the occurrence of the one or more sleep-related event corresponds with at least a need for the pressure support therapy;
         determine, via the communications unit in wireless communication with the pressure support device, immediately before, during, and immediately after the occurrence of the one or more sleep-related event, a condition of the pressure support device, wherein determining immediately before the occurrence of the one or more sleep-related events comprises determining that a predetermined bed time for the user will be occurring within a predetermined period of time, and that the pressure support device is within a predetermined proximity of the wearable smart device but not turned on; and
         provide, via the output device, an actionable guidance indication responsive to the determined occurrence and the determined condition corresponding with (i) the pressure support therapy is needed, (ii) a sleep-related event of the user is falling asleep or is having been awaken from sleep for which the user is likely to accept actionable guidance, and (iii) the pressure support device is located within a given proximity to the wearable smart device, wherein the actionable guidance indication comprises one or more of the audible alert, the vibratory alert, and the visual alert configured to increase the user adherence to the pressure support therapy.

13. The system of claim 12, wherein the one or more user attributes comprise at least one of actigraphy or heart rate.

14. The system of claim 12, wherein the communications unit is structured to wirelessly communicate with the pressure support device via a Bluetooth™ standardized protocol for sending and receiving data via a wireless link.

15. The external wearable smart device of claim 10, wherein collecting data regarding the number of user attributes comprises collecting data regarding one or more of: actigraphy, heart rate, and/or oxygen saturation of the user and respective time information thereof.

16. The external wearable smart device of claim 10, wherein determining the occurrence of the sleep-related event further comprises determining one or more of: the user is trailing toward sleep; the user is sleeping; and the user is experiencing a sleep disruption.

17. The external wearable smart device of claim 10, wherein determining the condition of the pressure support device comprises determining that the pressure support device is (i) one of turned on and in use or (ii) not turned on.

18. The external wearable smart device of claim 10, wherein determining the condition of the pressure support device further comprises determining that the pressure support device is one of: (i) not within a predetermined proximity of the external wearable smart device; or (ii) within the predetermined proximity of the external wearable smart device, turned on and in use.

19. The external wearable smart device of claim 10, wherein determining the occurrence of the sleep-related event based on the collected data comprises determining a sleep onset for the user and an occurrence of a sleep disruption event for the user; wherein determining the condition of the pressure support device comprises a determination that the pressure support device is not in use; and
   wherein providing the actionable guidance indication to the user responsive to the determined occurrence and the determined condition further comprises providing an audible alert and a visual alert as actionable guidance for the user to use the pressure support device.

20. The external wearable smart device of claim 10, further comprising one selected from the group consisting of:
   (a) wherein determining the condition of the pressure support device further comprises a determination that the pressure support device is not within a predetermined proximity of the wearable smart device; and wherein providing the actionable guidance indication to the user further comprises displaying a visual reminder as actionable guidance for the user to obtain, within the predetermined period of time prior to the predetermined bed time, the pressure support device for use during sleep;
   (b) wherein determining the condition of the pressure support device further comprises a determination that (i) the pressure support device is within a predetermined proximity of the wearable smart device and (ii) the user has not used the pressure support device within a second predetermined period of time; and wherein providing the actionable guidance indication to the user further comprises displaying, via the output device, a visual reminder as actionable guidance for the user to use the pressure support device within the second predetermined period of time; and
   (c) wherein determining the occurrence of the sleep-related event based on the collected data further comprises a determination that the user is trailing toward sleep; wherein determining the condition of the pressure support device further comprises a determination that the pressure support device is not in use; and wherein providing, via the output device, the actionable guidance indication to the user further comprises providing the one or more of: the audible alert, the vibratory alert, and the visual alert.

* * * * *